US007015232B2

(12) United States Patent
Daniel et al.

(10) Patent No.: US 7,015,232 B2
(45) Date of Patent: Mar. 21, 2006

(54) STABILIZATION OF QUINAPRIL USING MAGNESIUM OXIDE

(75) Inventors: Jane Ellen Daniel, Verona, NJ (US); Michael Ray Harris, Hackettstown, NJ (US); Gerard Clifford Hokanson, Long Valley, NJ (US); Jay Weiss, East Brunswick, NJ (US)

(73) Assignee: Warner-Lambert Company, LLC, Morris Plains, NJ (US)

( * ) Notice: Subject to any disclaimer, the term of this patent is extended or adjusted under 35 U.S.C. 154(b) by 0 days.

(21) Appl. No.: 10/127,181

(22) Filed: Apr. 22, 2002

(65) Prior Publication Data

US 2002/0161020 A1 Oct. 31, 2002

Related U.S. Application Data

(62) Division of application No. 09/700,883, filed as application No. PCT/US99/10189 on May 10, 1999, now Pat. No. 6,417,196.

(60) Provisional application No. 60/088,280, filed on Jun. 5, 1998.

(51) Int. Cl.
 *A61K 31/47* (2006.01)
(52) U.S. Cl. ...................... 514/310; 514/423; 514/562; 424/440; 424/465
(58) Field of Classification Search ................ 514/310, 514/423, 562; 424/440, 465
See application file for complete search history.

(56) References Cited

U.S. PATENT DOCUMENTS

| | | | |
|---|---|---|---|
| 3,320,029 A | 5/1967 | Adams | |
| 4,344,949 A | 8/1982 | Hoefle et al. | |
| 4,374,829 A | 2/1983 | Harris et al. | |
| 4,425,355 A | 1/1984 | Hoefle et al. | |
| 4,743,450 A * | 5/1988 | Harris et al. | ............... 424/440 |
| 4,793,998 A | 12/1988 | Murthy et al. | ............... 424/440 |
| 4,830,853 A | 5/1989 | Murthy et al. | ............... 424/440 |
| 5,603,943 A | 2/1997 | Yanagawa | |
| 5,622,985 A | 4/1997 | Olukotun et al. | |
| 5,780,057 A | 7/1998 | Conte et al. | |
| 6,531,486 B1 * | 3/2003 | Sherman | ................... 514/307 |

FOREIGN PATENT DOCUMENTS

| | | |
|---|---|---|
| EP | 0 468 929 A2 | 7/1990 |
| EP | 468929 B1 * | 1/1992 |
| EP | 526862 A1 * | 2/1993 |
| EP | 468929 A | 9/1994 |

OTHER PUBLICATIONS

Captopril, Entry 1817, The Merck Index, 12th Edition, p. 288-289 (1996).
Univasc Product Information Brochure posted @ http://www.schwarzusa.com (1998).
Rex N. brogden, et al., Moexipril—A review of its use in the management of essential hypertension, Adis Drug Eval., Drugs., Jun., 55(6): 848-860 (1998).
"Everything You Ever Wanted To Know About Magnesium Oxide", Martin Marietta Magnesia Specialties posted @ http://magspecilaties.com/students.htm (2001).

* cited by examiner

*Primary Examiner*—Dwayne C. Jones
(74) *Attorney, Agent, or Firm*—William R. Boudreaux; Charles W. Ashbrook

(57) ABSTRACT

The present invention is directed to ACE inhibitor-containing compositions stabilized by the presence of magnesium oxide. Preferably, the ACE inhibitor, quinapril, is protected from certain forms of degradation when prepared in a pharmaceutical composition consisting essentially of magnesium oxide as the stabilizing agent. The presence of magnesium oxide also lends itself to favorable processing conditions during the manufacture of ACE inhibitor-containing compositions, especially processing by wet granulation.

2 Claims, No Drawings

STABILIZATION OF QUINAPRIL USING MAGNESIUM OXIDE

This application is a division of Ser. No. 09/700,883 filed Nov. 20, 2000 now U.S. Pat. No. 6,417,196 which is a 371 of PCT/US99/10189 filed May 10, 1999 which claims benefit of U.S. provisional application 60/088,280 filed Jun. 5, 1998.

FIELD OF THE INVENTION

The present invention is directed to ACE inhibitor-containing compositions stabilized by the presence of magnesium oxide. Preferably, the ACE inhibitor, quinapril, is protected from certain forms of degradation when prepared in a pharmaceutical composition consisting essentially of magnesium oxide as the stabilizing agent. The presence of magnesium oxide also lends itself to favorable processing conditions during the manufacture of ACE inhibitor-containing compositions, especially processing by wet granulation.

BACKGROUND OF THE INVENTION

Certain ACE (Angiotensin Converting Enzyme) inhibitors, which are useful as antihypertensives, are susceptible to certain types of degradation. Specifically, quinapril and structurally-related drugs can degrade via (1) cyclization via internal nucleophilic attack to form substituted diketopiperazines, (2) hydrolysis of the side-chain ester group, and (3) oxidation to form products having often unwanted coloration.

U.S. Pat. No. 4,743,450 discloses that stable compositions containing ACE inhibitors of the type discussed above can be produced using certain additives as stabilizers. Specifically, this patent discloses that the inorganic salts of metals of Group I and II of the Periodic Table act as stabilizers of ACE inhibitor-containing formulations susceptible to certain types of degradation. Magnesium carbonate is taught to be a preferred stabilizer.

One ACE inhibitor, quinapril HCl, is sold commercially under the tradename, ACCUPRIL®, and employs magnesium carbonate hydroxide in its formulations. Magnesium carbonate hydroxide contains approximately 40% to 42% magnesium oxide.

While magnesium carbonate hydroxide acts as an effective stabilizer of quinapril, its use in pharmaceutical formulations represents certain disadvantages. Magnesium carbonate hydroxide is a white, bulky powder which is difficult to formulate into tablets because of its poor compressibility, moldability, and flowability. The difficulties encountered by the use of magnesium carbonate hydroxide to formulate ACE inhibitor-containing compositions is accentuated when the compositions are manufactured using a wet granulation process.

The preparation of granulations for tableting by wet granulation is the oldest and still the most widely used. Before dry compaction became a viable process, wet granulation was—for all practical purposes—the only method available. However, it is laborious, involving considerable material handling, as well as several processing steps, and therefore it is costly. In general, the technique involves no more than the incorporation of a granulating fluid into the mixed, powdery tablet ingredients (including at least some tableting aids) in such an amount and manner as to convert them into a uniform, moist, coherent, non-pasty mass, which then is formed into moist granules of fairly uniform size, usually by forcing the mass through a screen. Thereafter, the moist granules are dried and rescreened to break down agglomerates, and finally blended with other tableting aids so as thus to arrive at the granulation ready for tableting.

It will be noted that in wet granulation, the tablet ingredients besides the active matter also conventionally include other, pharmacologically inert materials, certainly tableting aids and perhaps also bulking agents. Some of such tableting aids may be included in the mixed, powdery ingredients before the granulating fluid is incorporated therein, while further tableting aids may be applied to the surfaces of the granules, and in between them, after the granules have been formed and before the granulate is passed to the tableting machine.

The labor and cost so characteristic of wet granulation processes are common when compounds like magnesium carbonate hydroxide are mixed with ACE inhibitors like quinapril HCl. Manufacturers have experienced several rate-limiting steps when processing magnesium carbonate hydroxide: batch sizes limited due to the lower density of magnesium carbonate hydroxide blends; granulation times of 15 minutes or longer; variability in granulation times of 15 to 37 minutes when using different lots of magnesium carbonate hydroxide; need for high amounts of water to achieve granulation end points and potentially long drying times based upon initial loss on drying in the range of 23 to 29% (loss on drying or "LOD" is a moisture determination test using heat to determine how much water or solvent is in a product); and limitations in flowability.

Magnesium carbonate hydroxide is also problematic to manufacturers because of sourcing concerns.

It can be understood that it would be an improvement to the art if one could improve the wet granulation processing conditions of an ACE inhibitor-containing formulation without sacrificing the stabilizing effects of a compound like magnesium carbonate hydroxide.

SUMMARY OF THE INVENTION

It has been discovered that stable compositions containing ACE inhibitors of the type discussed above can be produced using magnesium oxide as the primary cyclization stabilizer. In one embodiment, a pharmaceutical composition is prepared by combining the ACE inhibitor, quinapril HCl, with a stabilizing agent consisting essentially of magnesium oxide. Use of magnesium oxide not only minimizes the cyclization degradation of ACE inhibitors, but also improves the formulation of ACE inhibitors into pharmaceutical compositions by the wet granulation technique. In a preferred embodiment, a pharmaceutical composition is prepared by combining the ACE inhibitor with not only a stabilizing agent consisting essentially of magnesium oxide, but also an agent that minimizes the hydrolysis of the ACE inhibitor, such as a saccharide, a diuretic, dicalcium phosphate or commonly known fillers having hydrolysis minimizing effects on the ACE inhibitor. In a more preferred, a pharmaceutical composition is prepared by combining 5.8% by weight of magnesium oxide with 5.8% weight of quinapril hydrochloride with the inclusion of 88.3% weight of lactose to yield a composition which withstands oxidative, hydrolytic, and cyclization degradation at 60° C. for 10 days.

In another embodiment, a process is disclosed for preparing stabilized ACE inhibitor-containing compositions with magnesium oxide. The process comprises the steps of contacting the ACE inhibitor with a suitable amount of a stabilizer consisting essentially of magnesium oxide and one or more hydrolysis-minimizing agents, such as saccharides, to minimize hydrolysis. In a preferred embodiment, the process comprises the steps of contacting quinapril HCl with a suitable amount of a stabilizer consisting essentially of magnesium oxide and one or more saccharides to form a mixture; and subjecting the mixture to wet granulation processing.

The compositions of the invention have several advantages over compositions which do not contain the stabilizing additive. Principally, the active ingredients or drugs contained therein are virtually protected from cyclization and hydrolysis. In addition, the discoloration which sometimes occurs when ACE inhibitors of this class are formulated and allowed to stand for significant periods of time is minimized or eliminated completely. Thus, a stable tabletted quinapril formulation can be produced which will undergo no detectable oxidative discoloration.

In addition to having greater storage stability, the formulations of the present inventions are rendered more suitable for use in drug combinations.

The instant formulations are further advantageous due to the fact that the presence of magnesium carbonate hydroxide, and all of its inherent disadvantages, is unnecessary. Preparation of ACE inhibitor-containing compositions with magnesium oxide as the principal stabilizer results in improved processing by a wet granulation technique. Improvements that decrease the cost and labor include, but are not limited to an increase in batch sizes due to the high density of magnesium oxide formulations; granulation times of 4.5 to 5 minutes or less; decreased variability in granulation times (between 0.5 to 1 minute) when using different lots of magnesium oxide; decreased amounts of water to achieve granulation end points and shorter drying times based upon initial loss on drying (LOD) values in the range of 5% to 8% and improved flowability.

These and other advantages of the invention will become apparent from a consideration of the following description of the invention.

DETAILED DESCRIPTION OF THE INVENTION

The invention deals with:
I. A pharmaceutical composition which contains:
 (a) an effective amount of a drug component which comprises an ACE inhibitor which is susceptible to cyclization, hydrolysis, and/or discoloration, and
 (b) an effective amount of magnesium oxide and a hydrolysis-minimizing agent suitable to retard cyclization, hydrolysis, and/or discoloration, wherein the magnesium oxide is the principal cyclization stabilizer component of the composition.
II. A process for stabilizing an ACE inhibitor drug which comprises the step of contacting the drug with:
 (a) an effective amount of magnesium oxide and a hydrolysis-minimizing agent suitable to retard cyclization, hydrolysis, and/or discoloration, wherein the magnesium oxide is the principal cyclization stabilizer component of the composition.
III. A method of making a pharmaceutical dosage form which comprises the step of including in the formulation suitable amounts of:
 (a) an ACE inhibitor, and
 (b) magnesium oxide and a hydrolysis-minimizing agent to retard cyclization, hydrolysis, and/or discoloration of the dosage form, the magnesium oxide acting as the principal cyclization stabilizer component of the dosage form.

Preferably, the compositions and processes made and used in accordance with the invention will also contain one or more substances which do not interfere with the function of the stabilizing additive(s). Generally, lubricants, such as magnesium stearate, hydrogenated vegetable oils and talc, binders, such as gelatin, and/or disintegrants, such as polyplasdone, are suitable.

Drug Component(s)

The compositions of the invention contain at least one ACE inhibitor and, optionally, one or more other medicament drugs or beneficial substances. The ACE inhibitors which can be used in the invention are any of a group of well-known compounds which have antihypertensive properties.

One preferred group of compounds includes compounds conforming to the general formula:

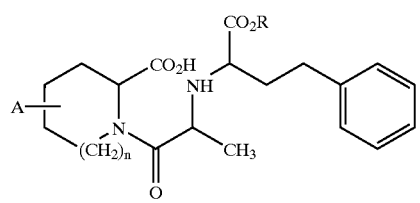

wherein A is absent, a fused 5-, 6-, or 7-membered cycloaliphatic ring or a fused benzene ring which is unsubstituted or substituted by 1 or 2 alkoxy groups having 1 to 4 carbon atoms; n is 0 or 1, and R is hydrogen or alkyl having 1 to 5 carbon atoms. Preferably A is absent, a fused 5- or 6-membered cycloaliphatic ring or a fused benzene ring which is unsubstituted or substituted by 2 methoxy groups; n is 0 or 1, and R is hydrogen or ethyl.

Particularly valuable are enalapril, quinapril, or indolapril, their corresponding free acids or pharmaceutically acceptable acid addition or base salts thereof. Compounds of this type are disclosed in U.S. Pat. Nos. 4,344,949, 4,374,829, and 4,425,355, the disclosure of which are hereby incorporated by reference.

The total drug content of the final composition will be about 1% to about 70%, preferably from about 1% to about 25%, and most preferably from about 5% to about 8%.

All percentages stated herein are weight percentages based on total composition weight, unless otherwise stated.

The daily dosages of the pharmaceutical preparations of the invention depend upon the nature of the dosage form, the nature of the drug(s), and the type and extent of any interactive(s) in drug combinations. Thus, the therapeutic needs of the individual patient and the desires of the prescribing physician dictate the dosage levels to be employed. In general, however, the manufacturer's specifications for any drug or drug combination are useful guides to administration. *The Physicians' Desk Reference* or other suitable publication can be consulted to ascertain appropriate dosage levels.

Nonetheless, typical dosage levels for quinapril and enalapril are from about 1 mg to about 80 mg per dosage.

Suitable categories of drugs that may be employed in addition to ACE inhibitors in the instant compositions may vary widely and generally represent any stable drug combination. Illustrative categories and specific examples include:

(a) Diuretics, such as hydrochlorothiazide, (b) Antitussives, such as dextromethorphan, dextromethorphan hydrobromide, noscapine, carbetapentane citrate, and chlophedianol hydrochloride, (c) Antihistamines, such as chlorpheniramine maleate, phenindamine tartrate, pyrilamine maleate, doxylamine succinate, and phenyltoloxamine citrate, (d) Decongestants, such as phenylephedrine hydrochloride, phenylpropanolamine hydrochloride, pseudoephedrine hydrochloride, and ephedrine, (e) Various alkaloids, such as codeine phosphate, codeine sulfate, and morphine, (f) Mineral supplements such as potassium chloride and the like.

The medicaments and/or other beneficial substances to be used herein may be selected from a wide variety of substances and pharmaceutically acceptable forms thereof, e.g., their acid addition salts. Both organic and inorganic salts may be used provided the drug maintains its medicament value. Exemplary acid salts include, but are not limited to, hydrochloride, hydrobromide, orthophosphate, benzoate, maleate, tartrate, succinate, citrate, salicylate, sulfate, acetate, and the like. Mixtures are operable.

One preferred group of drugs to be used in combination with ACE inhibitors includes: betablockers, diuretics, calcium blockers, and the like.

Stabilizer(s)

The cyclization and hydrolytic instability which are exhibited by certain of the drugs discussed above can be overcome via the use of a suitable quantity, i.e., an effective amount of magnesium oxide together with a an agent that minimizes the hydrolysis of the ACE inhibitor, such as saccharides. While additional stabilizers may be present in the present invention, their cyclization stabilizing effects on the ACE inhibitor formulations are minimal in comparison to the stabilizing effects of the magnesium oxide. Even small amounts of magnesium carbonate, which can result from the exposure of magnesium oxide to water and air, will have a minimal stabilizing effect on the ACE inhibitor formulations when compared to the stabilizing effect of the magnesium oxide present in the formulation.

Magnesium oxide, or calcined magnesia, is commercially available from such companies as Dead Sea Periclase of Israel, Lohmann of Germany or Morton International. This compound occurs in nature as the mineral periclase. Commercial preparation of magnesium oxide from magnesite ores is described in U.S. Pat. No. 3,320,029.

Magnesium oxide is available in many commercial grades, all of which are within the scope of the present invention. Two preferred forms of magnesium oxide are a very bulky form termed "Light" and a dense form termed "Heavy."

In the preferred embodiment of the invention, the stabilized ACE-inhibitor compositions consist essentially of magnesium oxide as the cyclization stabilizer. The quantity of the magnesium oxide to be used will lie between about 1% and 90%, preferably about 1% to about 50%, and most preferably about 1% to about 10% of the total composition. In general, any amount which will effectively retard or prevent cyclization degradation of the ACE inhibitor component(s) can be used.

Hydrolysis-Minimizing Agent

The hydrolysis-minimizing agents of the present invention act to protect the ACE inhibitor from hydrolytic degradation. The hydrolysis-minimizing agent(s) to be used in the pharmaceutical products and methods of the invention are substances which are compatible with magnesium oxide so that they do not interfere with magnesium oxide's function in the composition. Generally, they are substances which do not contain groups which could significantly interfere with the function of either the metal-containing component or the drug component. Preferred hydrolysis-minimizing agents of the present invention are saccharides such as mannitol, lactose, and other sugars, diuretics, dicalcium phosphate, hydrochloro thiazide, and known fillers that have a hydrolysis-minimizing effect on the ACE inhibitors. Saccharides are most preferred and mixtures are operable.

Generally, the quantity of the hydrolysis-minimizing agent present will be from about 10% to about 95%, preferably about 50% to about 95%, and most preferably from about 70% to about 90% of the total composition.

Dosage Forms

The compositions of the present invention can be administered to a patient alone or as part of a composition that contains other components such as excipients, diluents, and carriers, all of which are well-known in the art. The compositions can be administered to humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

The final form of the pharmaceutical preparations made in accordance with the invention can vary greatly. Orally administrable forms, i.e., tablets, caplets, and capsules, are preferred. Solid, semi-solid, and liquid formulations can be made. However, solids are highly preferred. The optional excipients which can be used in the instant compositions are also substances which must be compatible with magnesium oxide so that it does not interfere with its function in the composition.

Compositions suitable for parenteral injection may comprise physiologically acceptable sterile aqueous or nonaqueous solutions, dispersions, suspensions, or emulsions and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), Cremophor EL (a derivative of castor oil and ethylene oxide; purchased from Sigma Chemical Co., St. Louis, Mo.) and suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, potato or tapioca starch, alginic acid, certain complex silicates, modified starch, polyvinylpyrrolidone (cross- or uncross-linked), and modified cellulose derivatives, (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; (i) lubricants, as for example, talc, hydrogenated vegetable oil, zinc stearate, calcium stearate, magnesium stearate, solid polyethylene glycols, sodium lauryl sulfate; (j) pigments; and (k) colorants or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, Cremophor EL (a derivative of castor oil and ethylene oxide; purchased from Sigma Chemical Co., St. Louis, Mo.), polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents. Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethylene glycol, or a suppository wax, which are solid at ordinary temperatures but liquid at body temperature and, therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The above ACE inhibitor-containing compositions set forth above will be used in therapeutic amounts as indicated in the Physicians' Desk Reference (PDR) 47$^{th}$ Edition (1993), which is incorporated herein by reference, or such therapeutically useful amounts as would be known to one of ordinary skill in the art.

The compositions can be administered at the recommended maximum clinical dosage or at lower doses. Dosage levels of the active compounds in the compositions of the invention may be varied so as to obtain a desired therapeutic response depending on the route of administration, severity of the disease, and the response of the patient. The determination of optimum dosages for a particular patient is well known to those skilled in the art.

Processing

The present invention is directed to a process for stabilizing an ACE inhibitor drug which comprises the step of contacting an effective amount of the drug with an effective amount of magnesium oxide and a hydrolysis-minimizing agent suitable to retard cyclization, hydrolysis, and/or discoloration, wherein the magnesium oxide is the principal cyclization stabilizer component of the composition. While any techniques known to those of skill in the art for contacting the drug and the magnesium oxide, and which are appropriate, can be employed, a wet granulation process is preferred. The presence of magnesium oxide lends itself to improved wet granulation processing of ACE inhibitor-containing compositions, the advantages of which are discussed below in detail in Example 6 where a comparison is made of previously known magnesium carbonate hydroxide formulations and the magnesium oxide formulations of the present invention. A summary of these advantages is as follows:

(1) magnesium oxide formulations are dense and can allow an increase in batch sizes using current equipment;
(2) a decrease in granulation times, the granulation times ranging from about 4.5 to about 5 minutes or less;
(3) a decrease in the variability in granulation times, the variability ranging from about 0.5 to about 1 minute when using different lots of magnesium oxide;
(4) a decrease in the amounts of water required to achieve granulation end points and potentially shorter drying times, the amounts of water required is from about 50% or less and drying times of about 7 minutes;
(5) initial LODs in the range of 5 to 8%;
(6) an improvement in the flowability or angle of repose test where magnesium oxide formulations had a flowability or angle of repose of 32°.

In a preferred embodiment, the present invention is directed to a process for preparing a stabilized pharmaceutical composition comprising an effective amount of an ACE inhibitor and a hydrolysis-minimizing agent and consisting essentially of an effective amount of magnesium oxide as the cyclization stabilizing agent, wherein the process comprises:

(1) blending together a suitable amount of an ACE inhibitor, a hydrolysis-minimizing agent and magnesium oxide;

(2) adding a granulating fluid to the blend to form a moist mass;

(3) drying the granules; and (4) blending the granules with pharmaceutically inactive excipients.

The process further comprises the optional steps of screening the dried granules before addition of the pharmaceutically inactive excipients. The granulation medicament so formed may then be subjected to further conventional processing to form various solid dosage forms. The solid dosage forms may then be processed into final dosage forms by conventional techniques.

The percentages in which excipients are used are not critical. In general, their quantities will be consistent with the amount given above for the drug and stabilizer components (disintegrant about 1% to about 15% of the total composition; lubricant about 0.1% to about 5% of the total composition; and binder about 1% to about 10% of the total composition), i.e., they make up the remainder of the composition.

The drug preparations can be adapted for immediate, slow, or sustained release profiles, or any combination of these. Thus, a formulation adapted to give an initial loading dosage within 30 minutes followed by sustained release of the remaining drug over 4 to 12 hours is contemplated. Sustained and immediate release formulations are preferred. Reasonable variations, such as those which would occur to a skilled artisan, can be made herein without departing from the scope of the invention.

The examples presented below are intended to illustrate particular embodiments of the invention, and are not intended to limit the scope of the specification or the claims in any way.

EXAMPLE 1

The following materials were processed by wet granulation method for the manufacture of 20-mg tablets.

| | |
|---|---|
| Quinapril Hydrochloride | 21.7 mg |
| Magnesium Oxide | 21.7 mg |
| Lactose | 254.3 mg |
| Gelatin | 6.4 mg |
| Polyplasdone | 12.8 mg |
| Magnesium Stearate | 3.2 mg |

EXAMPLE 2

The following materials were processed by wet granulation for the manufacture of 5-mg tablets without the addition of a stabilizer.

| | |
|---|---|
| Quinapril Hydrochloride | 5.425 g |
| Lactose Anhydrous | 119.575 g |
| Microcrystalline Cellulose | 14.775 g |
| Disodium EDTA | 0.225 g |
| Sterotex HM | 1.500 g |
| Syloid 244 Silica Gel | 3.000 g |

-continued

| | |
|---|---|
| Stearic Acid | 4.500 g |
| Ascorbic Acid USP | 1.000 g |
| Water, Purified USP | 2.250 g |

EXAMPLE 3

The following materials were processed by wet granulation for the manufacture of 20-mg tablets without the addition of a stabilizer of the present invention.

| | |
|---|---|
| Quinapril Hydrochloride | 21.7 mg |
| Magnesium Carbonate Hydroxide | 125.0 mg |
| Lactose | 33.3 mg |
| Gelatin | 10.0 mg |
| Polyplasdone | 8.0 mg |
| Magnesium Stearate | 2.0 mg |

EXAMPLE 4

Stability of the tablets prepared in Examples 1 and 3 were tested at 60° C. for 10 days. The data shows that the use of magnesium oxide effectively stabilizes ACE inhibitor-containing compositions such as quinapril HCl compositions when compared against similar formulations that do not contain a stabilizer (Example 2) or contain magnesium carbonate hydroxide (Example 3). The data not only shows that magnesium oxide stabilizes ACE inhibitor-containing compositions as well as magnesium carbonate hydroxide, but also that the magnesium oxide formulation requires less gelatin (about 2%) than the magnesium carbonate hydroxide formulation (about 5%) to obtain acceptable compressability.

| | | Degradation Products (%) | |
|---|---|---|---|
| | Quinapril (%) Initial/10 Days | Diketopiperazine | Hydrolysis Product |
| Example 1 | 98.7/98.9 | — | — |
| Example 2[a,b] | 68.1 | 32.4 | <1 |
| Example 3 | 97.7/96.1 | — | — |

[a]Percent of original quinapril content
[b]Analysis was carried out after 1 month at 60° C.

EXAMPLE 5

Quinapril formulations containing magnesium oxide and quinapril formulations containing magnesium carbonate hydroxide were prepared for comparison in wet granulation processing. The formulations (1.5 kgs MgO and 1.5 kgs $MgCO_3$) were prepared by combining the following ingredients:

| | | |
|---|---|---|
| Quinapril HCl | 162.5 g | 101.7 g |
| Magnesium Oxide | — | 101.7 g |
| Magnesium Carbonate Hydroxide | 937.5 g | — |
| Lactose | 250.0 g | 1191.6 g |

-continued

| | | |
|---|---|---|
| Gelatin | 75.0 g | 30.0 g |
| Polyplasdone | 60.0 g | 60.0 g |
| Magnesium Stearate | 15.0 g | 15.0 g |

Results

The magnesium oxide formulations were denser than the magnesium carbonate hydroxide formulations. 2.5 kgs of the magnesium oxide formulations were able to be granulated in a 10 L Gral when compared to 1.5 kgs of magnesium carbonate hydroxide formulations. The bulk density of the blends prior to the addition of the gelatin solution was 0.70 g/mL for quinapril/magnesium oxide and 0.27 g/mL for quinapril/magnesium carbonate hydroxide.

The granulation time was shorter (4.5 to 5 minutes) with the magnesium oxide formulations compared to magnesium carbonate hydroxide formulations (15 to 37 minutes).

The variability in granulation times was decreased; about 15 to 17 minutes using different lots of magnesium carbonate hydroxide and 0.5 to 1 minute using different lots of magnesium oxide.

The quantity of water used to achieve granulation end point was decreased; magnesium oxide used 50% less water than magnesium carbonate hydroxide formulations.

The initial LOD for the magnesium oxide formulations was in the range of 5% to 8% compared to 23% to 29% for the magnesium carbonate hydroxide formulations.

The magnesium oxide formulations dried faster (7 minutes) than the magnesium carbonate hydroxide formulations (15–18 minutes).

A second wet milling step was avoided in the magnesium oxide formulations because no lumps with moisture in them were observed unlike the magnesium carbonate hydroxide formulations.

The flowability or angle of repose test indicated that the magnesium oxide formulations had better flowability (32° angle of repose) than the magnesium carbonate formulations (35° angle of repose).

Only one formulation containing magnesium oxide was necessary to deliver or manufacture quinapril HCl in four strengths (5, 10, 20 and 40 mg) compared to the two formulations required to deliver quinapril HCl in 5/10 mg and 20/40 mg strengths.

What is claimed is:

1. A pharmaceutical composition which contains:
   (a) quinapril hydrochloride;
   (b) a suitable amount of a stabilizer to retard cyclization and discoloration of quinapril, the stabilizer consisting essentially of magnesium oxide;
   (c) a suitable amount of a hydrolysis-minimizing agent to inhibit hydrolysis, the hydrolysis minimizing agent consisting of lactose;
   (d) gelatin;
   (e) polyplasdone; and
   (f) magnesium stearate.

2. The pharmaceutical composition of claim 1, wherein quinapril hydrochloride, magnesium oxide, lactose, gelatin, polyplasdone, and magnesium stearate are used in the following percentages:

| | Percent Total Composition |
|---|---|
| Quinapril HCl | 7% |
| Magnesium Oxide | 7% |
| Lactose | 79% |
| Gelatin | 2% |
| Polyplasdone | 4% |
| Magnesium Stearate | 1% |
| | 100%. |

* * * * *